(12) United States Patent
Sutter

(10) Patent No.: US 8,518,033 B2
(45) Date of Patent: Aug. 27, 2013

(54) CUTTING AND COAGULATION ELECTRODE

(75) Inventor: Bert Sutter, Freiburg (DE)

(73) Assignee: Sutter Medizintechnik GmbH, Freiburg (DE)

( * ) Notice: Subject to any disclaimer, the term of this patent is extended or adjusted under 35 U.S.C. 154(b) by 826 days.

(21) Appl. No.: 12/327,297

(22) Filed: Dec. 3, 2008

(65) Prior Publication Data

US 2009/0171352 A1 Jul. 2, 2009

(30) Foreign Application Priority Data

Dec. 28, 2007 (DE) .......................... 10 2007 062 939

(51) Int. Cl.
*A61B 18/18* (2006.01)

(52) U.S. Cl.
USPC .................................. 606/37; 606/48; 606/50

(58) Field of Classification Search
USPC ......... 604/32, 34, 37–41, 45, 48–50; 606/32, 606/34, 37–41, 45, 48–50
See application file for complete search history.

(56) References Cited

U.S. PATENT DOCUMENTS

| 3,987,795 | A | * | 10/1976 | Morrison | ........................ 606/48 |
| 4,202,337 | A | | 5/1980 | Hren et al. | |
| 5,282,799 | A | | 2/1994 | Rydell | |
| 5,702,390 | A | * | 12/1997 | Austin et al. | ..................... 606/48 |
| 5,944,718 | A | * | 8/1999 | Austin et al. | ..................... 606/48 |
| 6,110,196 | A | | 8/2000 | Edwards | |
| 6,832,998 | B2 | | 12/2004 | Goble | |
| 6,942,662 | B2 | | 9/2005 | Goble et al. | |
| 7,147,637 | B2 | | 12/2006 | Goble | |
| 7,195,630 | B2 | | 3/2007 | Ciarrocca | |
| 7,255,696 | B2 | | 8/2007 | Goble et al. | |
| 2003/0040744 | A1 | | 2/2003 | Latterell et al. | |
| 2005/0283149 | A1 | | 12/2005 | Thorne et al. | |
| 2005/0283151 | A1 | | 12/2005 | Ebbutt et al. | |
| 2007/0049921 | A1 | * | 3/2007 | Konishi et al. | ................... 606/37 |
| 2008/0103494 | A1 | * | 5/2008 | Rioux et al. | .................... 606/37 |
| 2010/0010485 | A1 | * | 1/2010 | West, Jr. | ........................ 606/37 |

FOREIGN PATENT DOCUMENTS

| DE | 4333983 | 4/1995 |
| DE | 20122382 | 7/2005 |
| DE | 102004026179 | 12/2005 |
| EP | 0795301 | 9/1997 |

* cited by examiner

*Primary Examiner* — Nicholas Lucchesi
*Assistant Examiner* — Nathan R Price
(74) *Attorney, Agent, or Firm* — Volpe and Koenig, P.C.

(57) ABSTRACT

In an electro-surgical instrument (1), two electrode surfaces (25, 27) are provided for a first electrode (15, 31, 32, 34, 36) having different sizes, each forming a pair of electrodes with electrode surfaces (26, 28) of a second electrode (14, 16, 33). The smaller electrode surface (25) of the first electrode (15, 31, 32, 34, 36) can be used as the active electrode for cutting and the larger electrode surface (27) of the first electrode (15, 31, 32, 34, 36) is used for coagulation. During operation, the electrodes (14, 15, 16, 31, 32, 33, 34, 36) are connected to a two-pole outlet of a commercial generator that can switch between two output signals for cutting and coagulation. A layered, stacked structure of the effective area (8) of the instrument (1) of electrode bodies (14, 15, 16, 31, 32, 33, 34, 36) with intermediate insulating layers (17) allows a design resembling the shape of a knife or a blade (11).

34 Claims, 4 Drawing Sheets

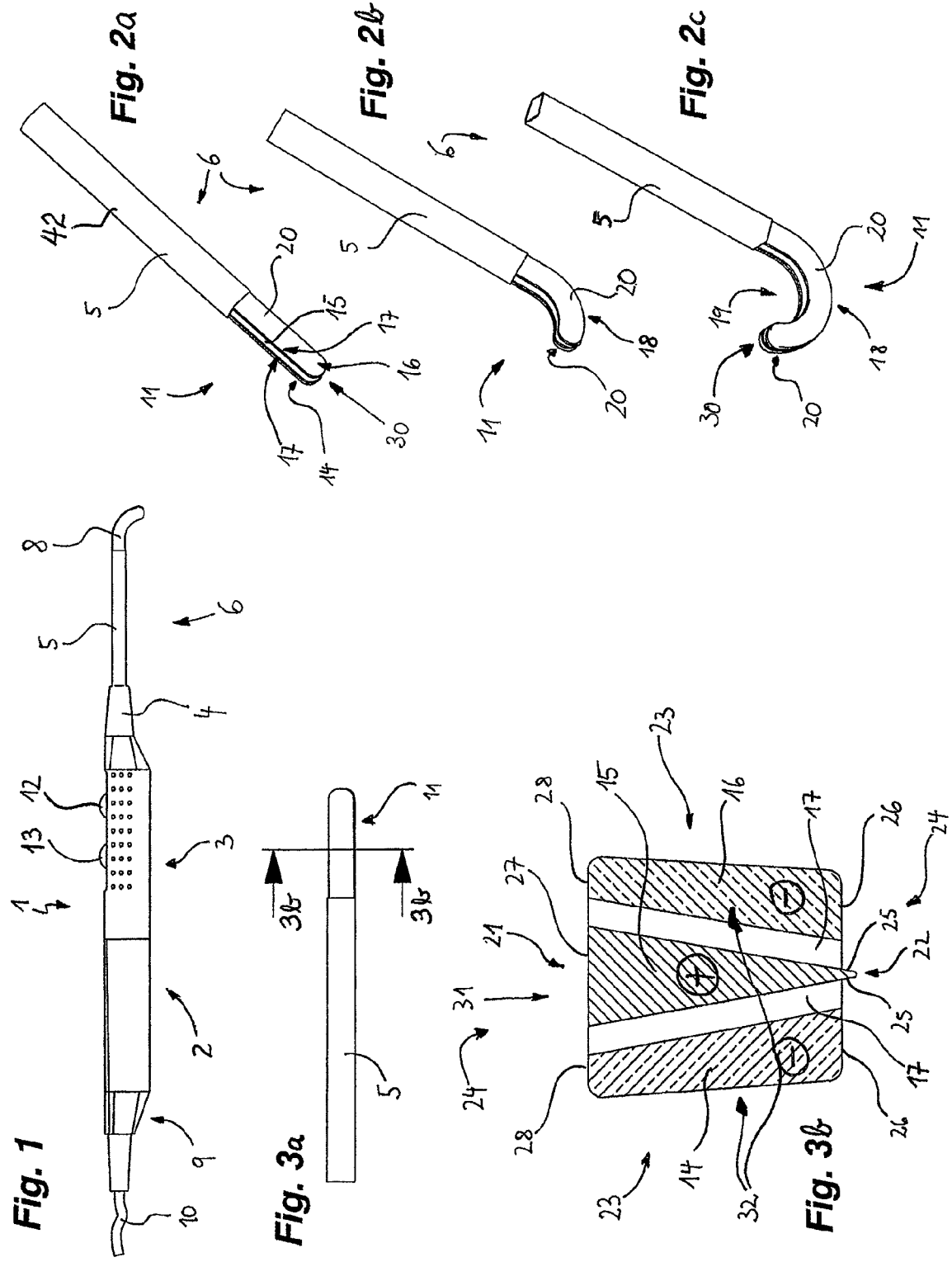

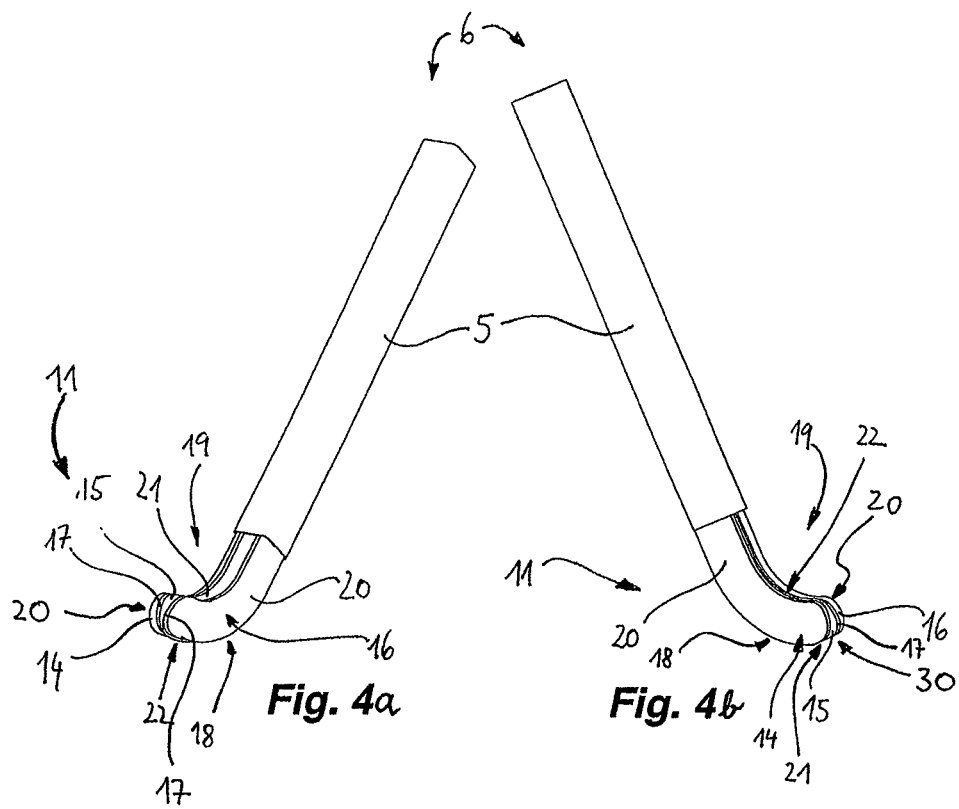
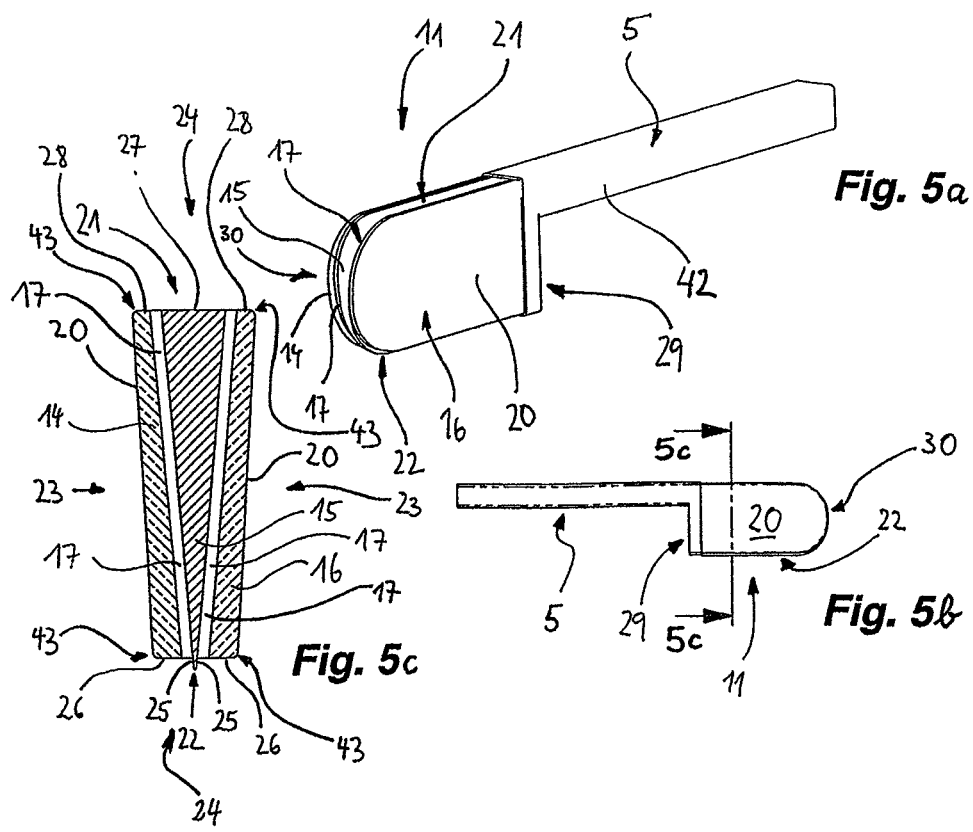

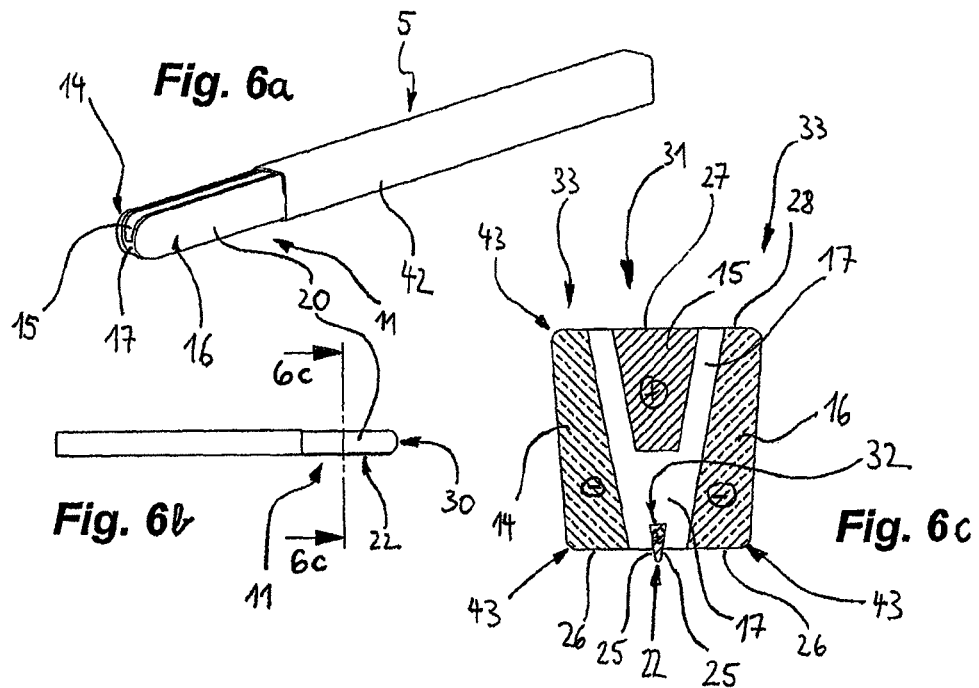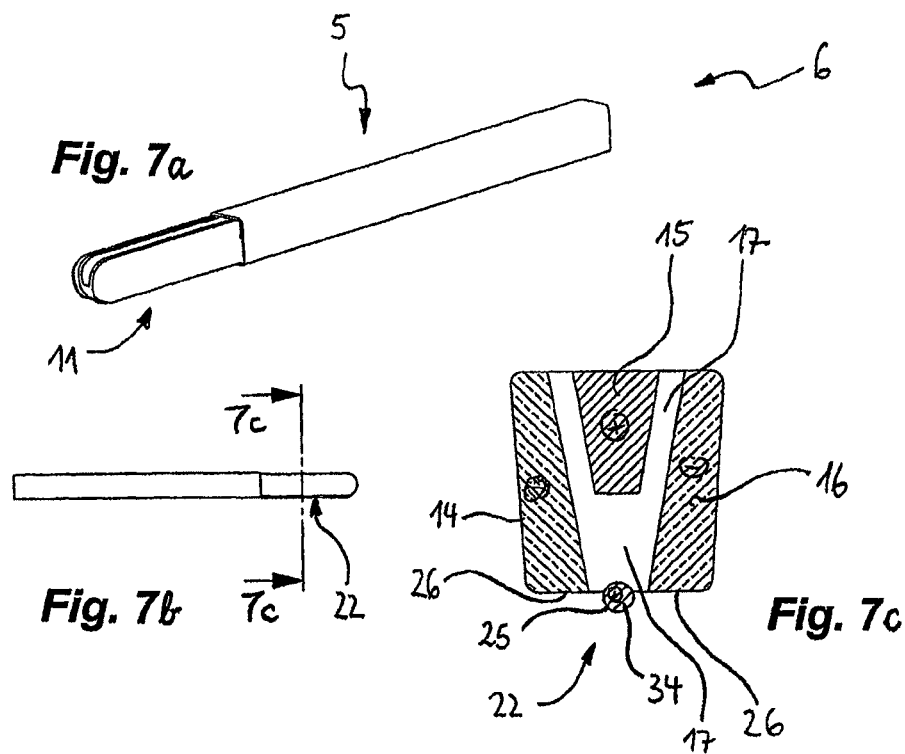

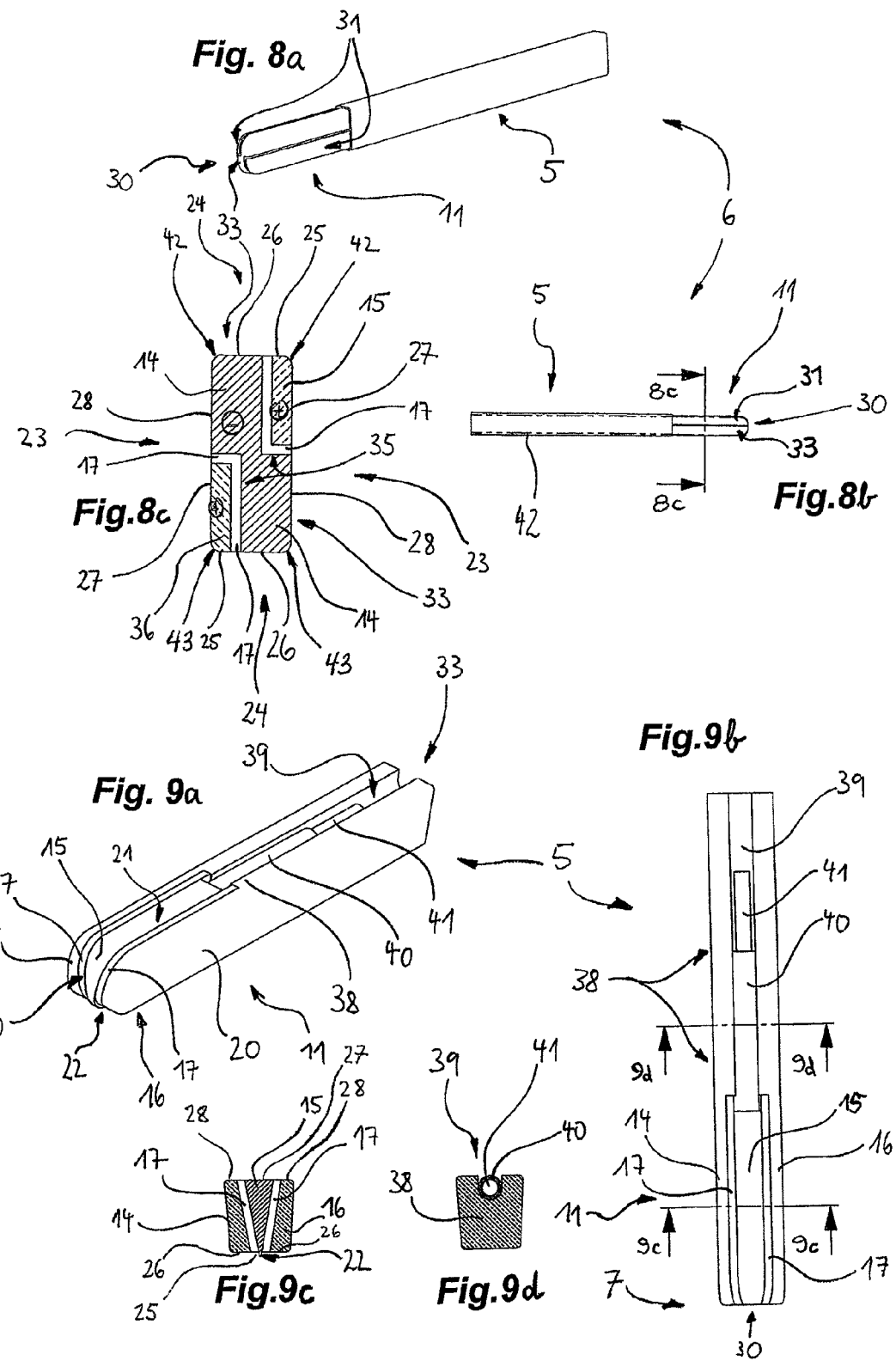

CUTTING AND COAGULATION ELECTRODE

CROSS-REFERENCE TO RELATED APPLICATIONS

This application claims the benefit of DE 10 2007 062 939.9, filed Dec. 28, 2007, which is incorporated herein by reference as if fully set forth.

BACKGROUND

The invention relates to an electro-surgical instrument for high-frequency cutting and high-frequency coagulation having two electrodes, spaced apart from each other by insulating material, particularly an insulating layer, which at the proximal end of the instrument are each connected during operation to an outlet of a high-frequency supply device, with a first electrode surface of a first electrode being designed such that together with the second electrode it can be used as the cutting electrode.

The cutting electrode is sometimes also called the active electrode. This is the electrode where preferably the electric current necessary for cutting ignites through the tissue.

Electro-surgical instruments with bipolar electrodes are known in many various embodiments.

They have been used for the coagulation of tissue for quite some time. This purpose is served, for example by bipolar tweezers or bipolar electrodes with poles fixed at a distance from each other and having approximately the same size, i.e. contact area to the tissue.

Bipolar electrodes are also known for electro-surgical cutting. In order to create a cut both electrodes coming into contact with the tissue must be of unequal sizes, i.e. embodied asymmetrically. In an asymmetrical embodiment the cut develops at the smaller electrode, which creates a spark by the higher current density and thus initiates the cut. Such an electrode arrangement is bad for coagulation, because by the development of sparks excessive temperatures are reached too fast. Coagulation electrodes in turn are unsuitable for cutting because by the equal size of the electrodes no particular high current density develops at either of the electrodes and thus no spark can develop.

An electrode particularly for bipolar cutting is described e.g., by Thorne et al. in US 2005/0283149 A1. Here, the cutting electrode is embodied in the form of a needle which is mounted in a hemispherical second electrode element and insulated therefrom. This arrangement can easily initiate a cut; however the coagulation of e.g., a vessel bleeding into the edge of the cut will hardly be possible.

A bipolar electrode in the form of knives is also described by Goble in U.S. Pat. No. 6,832,998 B2 for bipolar cutting. Here, a bigger and a smaller electrode are arranged beside each other and separated by an insulator. Furthermore, it is explained that the two electrodes are not only be different with regard to their size, but also with regard to their constitution, particularly their thermal conductivity. This further favors the simplicity and regularity of the cut at the smaller electrode. This electrode arrangement is also rather unsuitable for coagulating tissue. In order to overcome this, U.S. Pat. No. 6,832,998 B2 points out that it may be advantageous to provide a third electrode on the knife, which is electrically insulated from the other two electrodes. However, here it is necessary for the electro-surgery—generator to be able to switch between the electrodes and thus to stop supplying the formerly "active" electrode with electric current, but instead to supply the third electrode with the counter pole of the first electrode in order to use two electrodes that are approximately equal in size for coagulation.

In U.S. Pat. No. 6,942,662 B2 Goble et al. once more discuss the necessity of a third electrode in order to allow also to coagulate via the bipolar cutting knife. Here again, a switching mechanism between the different pairs of electrodes, installed in the generator, is a requirement for the operation of said instrument.

In a modification thereof, Goble discusses in U.S. Pat. No. 7,147,637 B2 a bipolar gripping or clamping instrument, with all electrodes being located on one of the two jaw parts and the second jaw part being completely electrically insulated at the gripping surface. Here again, the arrangement requires three electrodes, and again a respective device must be provided in the generator to switch back and forth between the electrodes.

In US 2005/0283151 A1 Ebbutt et al. discuss a bipolar cutting knife, which largely resembles in its shape a classic knife. Here, a circumferentially extending thin electrode, representing the active electrode, cuts against the electrodes arranged on the two sides of the knife representing the passive electrodes. Here it is again provided to achieve a planar coagulation by placing one of the two sides of the knife onto the tissue so that a total of three electrodes are provided, with once more the two electrodes arranged on the area not connected to the third cutting electrode being activated, which in turn requires a switching mechanism in the generator.

In U.S. Pat. No. 7,255,696 B2 Goble et al. describe a bipolar cutting and coagulation instrument in form of a hook. Again, three electrodes are provided on the instrument, in which the same restrictions apply as in similar arrangements already in circulation. Additionally, in U.S. Pat. No. 7,255,696 a liquid circuit is provided inside the head of the electrode, which cools the two large-area electrodes.

In U.S. Pat. No. 6,110,196 Mueller et al. describe a bipolar cutting instrument, with the two electrodes being arranged one behind the other along an axis according to the direction of cutting. This can occur, e.g., by a loop-shaped wire electrode, which is interrupted at one point located in the direction of cutting and is electrically divided into two parts. It may also occur by a wire positioned circumferentially around a ceramic knife, which in turn is interrupted at one point and with the two wire elements representing the two electrodes. Coagulation can hardly be achieved with such an arrangement because the surface of the electrodes is very small and thus the current density at the electrodes is so high that a cutting rather than a coagulating effect is yielded. Additionally, the coagulation zone would be so small that sufficient closure of vessels would be impossible even in cases of relatively small vessel diameters. Furthermore, during the cutting process the thin electrodes heat up, which is not hindering the cutting process per se, however during coagulation it rapidly leads to a layer of denaturized protein, acting as an insulator, precipitating on the electrodes and thus the effectiveness of the coagulation is further reduced. In order to overcome this, Mueller et al. suggest, for example, to arrange two electrodes (e.g., by metal-coating a ceramic surface) on the back of a so-called carrier element in order to allow coagulation to be carried out by rotation of the instrument and the placement of this surface in the area to be affected. It must be expected once more that the coagulation electrodes heat very quickly due to the low material mass thereof in this design the coagulation remains insufficient. Furthermore it is necessary to provide additional electrodes, not connected in one piece to the cutting electrodes, on an insulating carrier element.

In US 2003/0040744 A1 Latterell et al. suggest a bipolar tubular instrument for cutting and coagulation. Once more an arrangement of three electrodes is used. Two of them form a hemisphere with a slot therebetween and are used for coagulation. In the slot itself, a third electrode is located in a displaceable fashion in the form of a hook, which can cut when active, while now the two other ones switched together acting as neutral. A mechanism is located inside the handles to displace the hook continuing in the tubular shaft. In this solution, once more a switching mechanism must be provided in the generator in order to allow the use of the instrument both for coagulation as well as for cutting. Furthermore, it is necessary to displace the described hook, which operates as the cutting electrode. Such a device renders the production of the instrument more expensive and still requires the user to manipulate the instrument in order to switch from cutting to coagulation and vice versa.

Rydell describes a bipolar tubular cutting instrument in U.S. Pat. No. 5,282,799. In another embodiment described a coagulation device is provided. Here, different than in Mueller et al. in U.S. Pat. No. 6,110,196, two parallel loops are used as electrodes. It is problematic here, that it is not clearly defined at which of the two loops the cut will begin, because due to the loops and thus the same current density the two electrodes are only activated when a different field distribution is enforced, and then the cutting starts. This can occur e.g., by placing first one of the two loops onto the tissue and then the second loop is brought closer. The cutting will then form at the second loop, because at the moment the second loop contacts the tissue here the electric field strength is greater than in the loop already located on the tissue. This aggravates the handling of the instrument and results in less precision during operation.

The U.S. Pat. No. 5,282,799 also describes an embodiment with additional large-area coagulation electrodes being applied proximally in reference to the two cutting loops on the insulator from which the loops exit, e.g., by way of metal-coating a ceramic surface. Here it is problematic that during placement of the two projecting loops onto the place to be coagulated they are obstructive as long as the loops project from the insulating body at the distal area. The distal end of a surgical instrument is called the patient-side end in this document, while the proximal end is the opposite end. In this document the surgical instrument is therefore considered the extended arm of the user, and the terms proximal and distal are understood and used in reference to the body of the user.

Furthermore, in the U.S. Pat. No. 5,282,799 the loops are electrically active and thus they develop either a coagulating effect or, due to their relatively small surface, perhaps even a cutting effect at another location of the tissue. In order to overcome this, U.S. Pat. No. 5,282,799 suggests retracting the loops into the insulating body. Although this facilitates the application of the coagulation electrodes, however it renders the production more expensive and burdens the user with a more complicated handling. Furthermore, the disadvantage remains that, as in the patent of Mueller et al. U.S. Pat. No. 6,110,196, the mass of the metal-coated coagulation electrodes is very small and that thus they would likely heat up very quickly and lead to insufficient coagulation.

Ciarrocca describes a bipolar coagulation and cutting electrode in U.S. Pat. No. 7,195,630 B2. Here, the surface of the two bipolar electrodes is increased and/or reduced, respectively, by a displaceable "converter element". For coagulation the "converter element" is made to contact the smaller of the two electrodes to enlarge its surface. The "converter element" is made to electrically contact the larger of the two electrodes for cutting, in order to enlarge it even further and thus to achieve a distinct asymmetry between one electrode and the other. This way the cut is created at the smaller electrode. U.S. Pat. No. 7,195,630 B2 only requires two electrodes, which are "converted" via a mechanical device into coagulation and/or cutting electrodes. However, for this purpose a mechanical device is necessary, rendering the production of the instrument more expensive and setting certain limits regarding the miniaturization of the instrument. Furthermore, only an essentially tubular instrument is described.

In U.S. Pat. No. 4,202,337, Hren et al. describe a bipolar electro-surgical knife. Here, a pole arranged circumferentially around a ceramic knife, the cutting electrode with a relatively small surface is used against the electrode elements applied on the flanks of the knife, which form the passive electrode. The passive electrodes on the flanks of the knife are applied in lines. Due to the fact that only two poles are provided either all electrode lines on the flanks of the knife combined form one electric pole or one or more of these lines are connected to the other pole, i.e. the cutting electrode. In the latter case, in turn, no electro-surgical cut will develop because by the switching of one of the electric lines of one or both of the flanks to the "active electrode," its surface, being in contact with the tissue, becomes so large that no spark will develop because the current density becomes too low. To this extent, the electrode arrangement is advantageous for cutting, however unsuitable for coagulation or vice versa.

Fleenor et al. describe a tubular bipolar cutting instrument in U.S. Pat. No. 5,484,435. It comprises two electrodes, one of which having a smaller surface than the second one so that the first one forms the active electrode and the second one the passive electrode. In this solution it is impossible to vary the size of one or both of the electrodes rendering the instrument limited to the electro-surgical cutting and thus subjecting it to the same limitations as e.g., the instrument described in US 2005/0283149 (Thorne et al.). In the aspect of a displaceable active electrode described, which may also be embodied as a hook, it resembles the instrument of US 2003/0040744 (Latterell et al), however, it differs therefrom in that only two electrodes are provided which is advantageous in that the instrument can be operated with any arbitrary generator, but is not very well suitable for the coagulation of tissue.

SUMMARY

The invention is based on the objective of providing an electro-surgical instrument that allows cutting and coagulation to be carried out electro-surgically, with it being easily and cost-effectively produced in an embodiment without any mechanical devices and possible to be operated with all common types of generators used.

This object is attained with an electro-surgical instrument according to the invention, in which a first electrode encompasses a second electrode surface, which can be used with the second electrode as the coagulation electrode, and that the effective area of the first electrode surface of the first electrode is smaller than the effective area of the second electrode surface of the first electrode.

In this document an electrode refers to all electrically conductive components of an electro-surgical instrument electrically connected to a common connector of the instrument. The electrodes can therefore be embodied in one piece or in several ones, with the individual components of the multi-part embodiment being connected to each other in an electrically conductive manner. Within the scope of this document, an electrode surface generally refers to the effective portion of an electrically conductive surface of an electrode, and the surface of the electrode may comprise one or more separate area sections, which in case of several area sections are connected in an electrically conductive manner. One electrode surface can be embodied as a part of a flat plane or as a general area having a curve or comprising edges or corners.

The first electrode according to the invention comprises two electrode surfaces, each individually forming a pair of electrodes together with the second electrode. According to a preferred embodiment, the pair of a first electrode surface of the first electrode and the second electrode is meant for cutting, with the first electrode being the active electrode, i.e. having the smaller effective electrode surface than the second electrode. With the formation of a second, larger electrode surface at the first electrode now an additional possibility for pairing the first electrode with the second electrode is provided, with the differences of the effective electrode surfaces being embodied smaller than in the first pairing. Thus, the additionally provided pair can be embodied and used for coagulation. The invention offers therefore the advantage that only two electrodes are necessary to allow both cutting as well as coagulation. Mechanical switches at the instrument interfering with the user or an electronically necessary switching of the output settings at the generator can be omitted, and, in particular, it can be used in commercial generators having two-pole outputs. For switching between cutting and coagulation the user at the most has to change the amplitude progression forms of the output signal at the generator, unless a common outlet signal for cutting and coagulation is considered sufficient. Thus, particularly during cutting, the cutting current also flows through the pair of electrodes for coagulation and during coagulation the coagulation current through the pair of electrodes for cutting.

It is beneficial when the second electrode comprises a first electrode surface, with its effective surface being larger than the effective surface of the first electrode surface of the first electrode and when the first electrode surface of the second electrode with the first electrode surface of the first electrode can be used as a neutral electrode during high-frequency cutting. The effective surface at an electrode refers to the portion of the area of the electrode primarily participating in coagulation or cutting, thus at which the essential portion of the electric flux lines of the coagulation or cutting current begins or ends. By the different sizes of the electrode surfaces provided, the start of the cutting process occurs at the first electrode, with the first electrode becoming the active electrode and the second electrode the neutral electrode.

Beneficial coagulation properties are achieved when a second electrode surface of the second electrode has an effective surface, essentially of equal size in reference to the effective surface of the second electrode surface of the first electrode, and when this electrode surface of the second electrode with the second electrode surface of the first electrode can be used as the pair of electrodes in high-frequency coagulation. A planar contact of both electrodes to the tissue is advantageous for coagulation, and both electrodes are equivalent, contrary to cutting. Good heating of the treated tissue section is important for coagulation so that the tissue temperature ranges from 60° C. to approximately 80° C. and the tissue is not overheated and charred.

A particularly compact embodiment is achieved when the first electrode surface of the second electrode and the second electrode surface of the second electrode are identical. Preferably the two electrode surfaces in this case convert into each other without any sharp separating lines, such as edges or the like, or the effective areas for cutting and coagulation are even identical.

A particularly robust embodiment is achieved when the first electrode surface of the first electrode and the second electrode surface of the first electrode are embodied at a common base body. For example, this base body may comprise an electrically non-conductive material with the electrode surfaces being applied on its surface in separate sections, for example by way of evaporation deposition or coating. An embodiment of the invention may provide for the base body of the first electrode to be embodied as an electrically conductive electrode body. First and second electrode surfaces are therefore embodied, at least partially, at the same electrically conductive, preferably metallic base body as the surface sections. It is particularly beneficial for the inactive surface sections of the electrode body to be covered by an insulating material or separated from the effective areas by the formation of edges.

A robust embodiment results when the first electrode surface of the second electrode and the second electrode surface of the second electrode are embodied at a common base body. Here, too, for example an electrically non-conductive, preferably ceramic or plastic, electrode body can be used advantageously, carrying the electrode surfaces in surface sections. The mounting of the electrode surfaces on the base body can be improved by connecting bars, extending through the base body and being embodied in one piece with the electrode surfaces. A particularly beneficial production of the base body of the second electrode results when the base body of the second electrode is embodied as an electrically conductive electrode body.

In one embodiment of the invention it may be provided that the first electrode is connected to the second electrode by at least one electrically insulating layer and the sandwich structure forms a knife of the electro-surgical instrument and that the layers of the sandwich structure are aligned longitudinally in reference to the sides of the knife. In this document a knife is generally considered a knife-blade shaped body with its edge, being equivalent to the blade of a knife, that may be embodied dull or rounded. This edge is also called the blade, even if it is not suitable for mechanical cutting or suitable to a limited extent only. The knife can be embodied with one blade or with two blades. These blades carry the effective sections, i.e. the electrode surfaces of the cutting process. By the formation of a knife, the surgeon or another user is provided with an instrument similar to the well known, mechanically cutting instrument. This way, a user of the instrument will always intuitively hold and use the instrument in the correct operating position. By the formation of at least one blade, the section of the instrument directly active during cutting is marked for the user. The connection of the layers of the sandwich structure can be improved by screws, rivets, or bars extending perpendicularly in reference to the directions of the layers. It is particularly beneficial when the bars are connected to the electrode surfaces of an electrode in an electrically conductive fashion and in one piece, and the insulating layer is molded around these bars.

A particularly well and universally applicable electro-surgical instrument results when the blade of the electro-surgical instrument is embodied like a spatula.

When the knife of the electro-surgical instrument is embodied saber-like or hook-shaped the instrument can additionally even accept or load tissue and subsequently cut or coagulate.

In one embodiment of the invention, it is provided that the knife has a back and a blade and that the back is wider than the blade. The individual sections of the knife, blade, side surfaces, and back, can be separated from each other by sharp edges, resulting in an approximately wedge-shaped cross-section or they can convert into each other via soft or rounded edges, thus forming an oval cross-section. Based on the geometric shape of the instrument the user can therefore easily recognize the blade being narrower in reference to the back and provided for electro-surgical cutting. By the formation of a back a larger area is provided, at which advantageously the electrode surfaces can be arranged for coagulation.

One embodiment of the invention provides that the first electrode surface of the first electrode is arranged at the exterior edge of the curved knife. Thus, the user can perform long cuts with the exterior edge by pulling. The interior edge can be embodied as a blade or as a coagulation surface.

Another embodiment provides that the first electrode surface of the first electrode is arranged at the interior edge of the curved knife. This way, the user can lift or load tissue with the instrument, for example a blood vessel, and subsequently separate it by electro-surgical cutting.

A particularly clear handling results when the first electrode surface of the first electrode and the second electrode surface of the first electrode are arranged at opposite edges of the knife. The sections of the instrument effective during cutting are thus clearly separated from the sections of the instrument effective during coagulation and the user changes from cutting to coagulation by rotating the instrument by 180° around its longitudinal axis.

A particularly simple handling results when the second electrode surface of the first electrode is arranged at least at one side of the knife. The user can therefore change from cutting to coagulation by pivoting the instrument by approximately 90° around the longitudinal axis of said instrument from a position perpendicular in reference to the tissue surface into a laterally contacting position, thus the virtual connecting line between the proximal and the distal end. This way, the cutting instrument can be changed by a simple, brief hand motion, in connection perhaps with a foot operation of the generator, into a coagulation instrument and vice versa. This way, during surgery the user is enabled to react quickly, rather error-free, and intuitively.

A particularly robust arrangement results when the side surfaces of the knife are formed at least partially by electrode bodies of the second electrode, because in this case the preferably metallic electrode body can accept the insulation layer located between them in a protective manner, carrying for example the more sensitive components of the first electrode.

A structure is produced in a particularly simple manner when the second electrode has two electrode bodies, preferably formed mirror-symmetrically in reference to each other, and when the two electrode bodies of the second electrode are arranged at both sides of the first electrode perpendicularly in reference to the longitudinal direction of the instrument. Thus the second electrode forms a seat for the first electrode having an insulating body. By the arrangement mirror-symmetrical in the cross-section it is achieved that neither of the two sides of the instrument is preferred, rather both sides of the instrument are equally effective. Thus, the user is not required to remember which of the externally similar sides has a certain functional property.

A particularly resistant cohesion of the instrument structure is achieved when the electrode bodies of the second electrode each form a prong of a one-piece, electrically conductive body in the shape of a tuning fork. The shape of a tuning fork usually defines a body with two legs being connected at one end, with the legs extending approximately parallel similar to the prongs of a tuning fork. Preferably the free ends of the prongs or legs of a tuning-fork shaped body are arranged at the distal end, while the section connecting the prongs or legs and perhaps a handle are embodied in the proximal end section of the instrument. The connecting section can be mechanically stressed and holds together the two electrode bodies of the two electrodes, thus forming a seat for the more filigree-shaped electrode bodies of the first electrode representing the active electrode during cutting.

A particularly beneficial embodiment is achieved when the first electrode describes the perimeter of a wedge in its cross-section, when a section around the acute edge of the wedge forms the first electrode surface of the first electrode, when the back of the wedge forms the second electrode surface, and when the first electrode is arranged between two electrode bodies of the second electrode. This forms the size ratio according to the invention between the first and the second electrode surface of the first electrode. The first electrode can be comprised from electrically conductive and electrically non-conductive sections to form the wedge-shaped cross-section. An embodiment with a particularly simple way of production results when the electrode bodies of the second electrode is connected in one piece, thus produced from a metallic or at least electrically conductive material.

In an advantageous embodiment of the invention it may be provided that the instrument has two opposite narrow sides and two flat sides arranged opposite in reference to each other, that a first narrow side forms an angle of 90° or less with a first flat side, and preferably encloses an angle less than 80°, that the flat sides are formed by one electrode body each of the second electrode, that these electrode bodies are each provided with electrode surfaces extending partially into the narrow sides, that the first electrode has an electrode body describing a wedge-shaped perimeter in its cross-section, that the electrode body of the first electrode is arranged between the electrode bodies of the second electrode and is spaced apart therefrom by insulating material, that an acute edge of the electrode body, wedge-shaped in its cross-section, projects from a narrow side, and that the back of the electrode body, wedge-shaped in its cross-section, forms a part of the opposite narrow side, so that a narrow side can cut and that the other narrow side can coagulate. The electrodes thus each form a pair of electrodes, with the connection lines inside the pairs being offset in reference to each other by a quarter rotation. By the embodiment of an angle less than 90° between a narrow side and a flat side, in a symmetrical design of the cutting central plane with regard to one of the narrow sides, a preferably conically tapering progression of the flat sides towards the other narrow side is achieved in the cross-section, by which the knife-shape of a mechanically cutting knife is resembled. Due to the fact that the second electrode extends into the narrow sides in which the electrode surfaces of the first electrode are arranged as well, the electro-surgically effective area is limited to the blade and the back of the instrument and, on the one hand, the user can precisely place the cut and, on the other hand, use the back for coagulating a large area.

Here, it is particularly beneficial when the electrode body of the first electrode is embodied in one piece and fills the perimeter, wedge-shaped in its cross-section.

A particularly well handling instrument with particularly good cutting properties results when the flat sides have an angle of less than 45°, preferably less than 25° in reference to each other. Preferably the back of the wedge-shaped electrode body of the first electrode is arranged at the first narrow side, because it represents the wider side in reference to the first narrow side, and for coagulation a placement and effect as large as possible is advantageous.

A pair of electrodes with particularly good cutting properties results when the first electrode surface of the first electrode describes at least a partially curved contour in the cross-section. The curved contour collects incoming electric flux lines in a small area, thus creating a large electric flux density causing a reliable ignition of the cutting current. Preferably the first electrode surface of the first electrode is embodied as one wire inserted in an insulating body or as the tip of a wedge-shaped base body.

The cutting properties are improved even further when the first electrode with its first electrode surface projects from the instrument body beyond the electrode surface of the second electrode used in high-frequency cutting, for example as a tip, sharp edge, or round wire.

In another exemplary embodiment of the invention it may be provided for the second electrode to comprise a base body having an essentially rectangular cross-section that the base body has at least one recess at a minimum of one edge, that an electrode body of the first electrode is inserted into said recess, separated from the second electrode by an insulating layer, that this electrode body of the first electrode has a first electrode surface, which forms a pair of electrodes for high-frequency cutting along the shorter side of the rectangle (together) with one side of the base body of the second electrode, and that the electrode body of the first electrode has a second electrode surface, which along the longer side of the rectangle forms a pair of electrodes for high-frequency coagulation (together) with another side of the base body of the second electrode.

An instrument that can be used at all four sides results when the instrument has two opposite narrow sides and two opposite flat sides, arranged off-set perpendicularly in reference thereto, each of which is formed at least partially by the narrow side and the flat side of a narrow electrode body of the first, cutting electrode when two such narrow electrode bodies are arranged off-set in reference to each other and when the electrode body of the second, neutral electrode extends approximately Z-shaped between the narrow electrode bodies and is spaced apart therefrom by insulating material, so that cutting can be performed with both narrow sides and coagulation with both flat sides. The electrode body of the second electrode, Z-shaped in its cross-section, is preferably produced in one piece from a metallic material and stabilizes the structure of the instrument under mechanical stress.

A particularly robust fastening of the electrode surfaces to the first electrode results when alternatively or additionally to the insulating layer, penetrating, connecting bars, rivets, screws, or the like connect the electrode bodies of the first electrode in one piece at the proximal end. Thus, a more massive embodiment results in sufficient stability at the proximal end, while at the distal end a place-saving, filigree, and light construction of the electrode surfaces ensure particularly good handling.

Particularly good coagulation properties result when the electrode surfaces of the first electrode effective during coagulation have a surface area ranging from two thirds to one and one half times the area of the electrode surface of the second electrode effective during coagulation. Preferably the surface area of the electrode surface of the first electrode effective during coagulation ranges from 0.9 to 1.1 times the surface area of the electrode surface of the second electrode effective during coagulation, although deviations therefrom can result by the selection of various materials, particularly with regard to the heat conductivity properties. Particularly advantageously, the electrode surface of the first electrode effective during coagulation has a surface area equivalent to the surface area of the electrode surface of the second electrode effective during coagulation.

Particularly advantageous conditions for cutting result when the electrode surface of the second electrode effective for cutting has a surface area amounting at least to one and one half times the surface area of the electrode surface of the first electrode effective during cutting. The general rule applies that the cutting properties, particularly the reliability of igniting the cutting current at the active electrode, is the greater the higher the ratio of the surface areas. Deviations can particularly result from the construction of the first electrode surface of the first electrode or by the material selection for the electrodes.

The electrodes of the electro-surgical instrument thus form a structural unity with the insulation layer, the electrodes of the electro-surgical instrument are therefore not mobile in reference to each other. Preferably the electrodes of the electro-surgical instrument are connected to a structural unit by the insulation layer.

BRIEF DESCRIPTION OF THE SEVERAL VIEWS OF THE DRAWINGS

The invention is now explained in greater detail using the figures, where functionally equivalent or similarly effective components are marked with the same reference character.

Shown in detail are:

FIG. 1 is a view of an electro-surgical instrument according to the invention,

FIG. 2a is a view of a spatula-shaped instrument insert for the instrument according to FIG. 1, FIG. 2b is a view of a saber-like curved instrument insert for the instrument according to FIG. 1, FIG. 2c is a view of a hook-shaped instrument insert for the instrument according to FIG. 1, FIG. 3a is a side view of a spatula-shaped instrument insert according to FIG. 2a, FIG. 3b is a cross-sectional view taken along 3b-3b in FIG. 3a, FIG. 4a is a view of an embodiment of an instrument insert formed in a curved manner having an exterior cutting edge, FIG. 4b is a view of another embodiment of an instrument insert formed in a curved manner having an interior cutting edge, FIG. 5a is a view of an instrument insert with extended flat sides, FIG. 5b is a side view of the instrument insert according to FIG. 5a, FIG. 5c is a cross-sectional view taken along 5c-5c in FIG. 5b, FIG. 6a is a view of an instrument insert with a divided first electrode, FIG. 6b is a side view of the instrument insert according to FIG. 6a, FIG. 6c is a cross-sectional view taken along 6c-6c in FIG. 6b, FIG. 7a is a view of an instrument insert with an inserted cutting wire in detail, FIG. 7b is a side view of the instrument insert according to FIG. 7a, FIG. 7c is a cross-sectional view taken along 7c-7c in FIG. 7b, FIG. 8a is a view of an instrument insert with a Z-shaped electrode body, FIG. 8b is a side view of the instrument insert according to FIG. 8a, FIG. 8c is a cross-sectional view taken along 8c-8c in FIG. 8b, FIG. 9a is a view of an instrument insert with an electrode body shaped like a tuning fork, FIG. 9b is a side view of an instrument insert according to FIG. 9a, FIG. 9c is a cross-sectional view taken at the distal end along 9c-9c in FIG. 9b, and FIG. 9*d* is a cross-sectional view taken at the proximal end along 9*d*-9*d* in FIG. 9*b*.

DETAILED DESCRIPTION OF THE PREFERRED EMBODIMENTS

FIG. 1 shows an electro-surgical instrument 1 according to the invention. The instrument 1 has an instrument body 2 with a handle 3 and an insert seat 4. The shaft 5 of an instrument insert 6 is placed and snapped into the insert seat 4. The effective area 8 of the instrument insert 6 is provided at the distal end 7 of the instrument 1, by which the instrument 1 coagulates and cuts.

A two-polar, shielded connection cable 10 is mounted at the proximal end 9 of the instrument 1 in FIG. 1, by which the instrument 1 can be connected to a generator, not shown in greater detail, and is supplied therefrom with a high-frequency cutting and/or coagulation voltage. The generator has a two-pole outlet to which the lines of the connection cable 10 are connected. Here, preferably frequencies of a range from 300 kHz and 2000 kHz or more are used and voltages of a few hundred Volts are connected so that during operation a power of up to a few hundred Watts is being consumed.

The control of the generator occurs via pedal buttons. Electric push button switches 13 are provided at the instrument for an additional control of the generator, for example via a forced short-circuit, and mechanic pedal buttons 12 for locking or ejecting the instrument insert 6.

For another exemplary embodiment both push buttons 13, 12 represent electrically acting push button switches, and the push button 13 is provided for the activation of the cutting current and the push button 12 for the activation of the coagulation current.

FIG. 2*a* shows an instrument insert 6, in which the effective area is embodied as a spatula-shaped knife 11. The knife 11 is formed in a sandwich-structure as a constructional unit comprising three electrode bodies 14, 15, and 16 with electrically insulating layers 17 positioned therebetween. These electrode bodies 14, 15, and 16 continue in the area of the shaft 5, in which they are encompassed by a plastic cover 42, thus encased, and held together. Inside the instrument body 2 the middle electrode body 15 is electrically connected to a line of the connection cable 10 and forms the first electrode of the instrument 1. The external electrode bodies 14 and 16 are electrically connected to each other in the area of the shaft 5 and inside the instrument body 2 to the second line of the connection cable 10. The exterior electrode bodies 14 and 16 thus jointly form the second electrode of the instrument 1.

FIG. 2*b* shows another instrument insert 6, in which the effective area 8 is embodied as a saber-like curved knife 11, thus guided in a curved manner. By the curvature the knife 11, an external edge 18 and an interior edge 19 are formed, each being connected by the lateral sides 20 of the knife 11. Similar to FIG. 2*a*, the knife 11 is constructed with a sandwich-like form from three electrode bodies 14, 15, and 16 with intermediate insulating layers 17 forming a structural unit, held together by the plastic cover 18 of the shaft 5. In the instrument insert 6 according to FIG. 2*b*, the central electrode body 15 is connected to a line of the connection cable 10, while the two exterior electrode bodies 14 and 16 are connected to another line of the connection cable 10.

FIG. 2*c* shows another exemplary embodiment of an instrument insert 6, in which the effective area 8 is embodied as a hook-shaped curved knife 11. This exemplary embodiment differs from the exemplary embodiment according to FIG. 2*b* in that the curved area of the knife 11 describes more than a quarter arc of a circle, rendering the distal end 7 of the knife 11 to point to the proximal end 9 of the instrument 1 in FIG. 1. The structure of the knife 11 resembles the description of FIGS. 2*a* and 2*b*. By the hook-shape a force can be applied to the received tissue by pulling the instrument 1 in the direction of the shaft 5.

FIG. 3*a* shows a side view of the spatula-shaped, thus straight embodied instrument insert 6 according to FIG. 2*a*.

FIG. 3*b* shows a cross-section through the knife 11 of the instrument insert 6 according to FIG. 3*a* along the section line A-A.

The electrode body 15 is embodied wedge-shaped in its cross-section and has a back 21 and an acute edge 22. The electrode body 15 carries an insulation layer 17 at each of its lateral surfaces, having a constant thickness and measured such that a voltage of a few hundred Volts, particularly from approximately 400 to 1500 V, no breakdowns occur. On the insulation layers 17 additional electrode bodies 14 and 16 are arranged towards the outside, to form a structural unit. The electrode bodies 14 and 16 are electrically connected. The first electrode is therefore formed by the electrode body 15 and in FIG. 3*b* and the following figures it is marked "+", the second electrode is jointly formed by the electrode bodies 14 and 16, and in FIG. 3*b* and the following figures they are each marked "−". The wedge shape of the electrode 15 is respectively formed by the electrodes 14 and 16 such that the knife 11 has two flat sides 23 as lateral surfaces, conically approaching each other in the direction of the wedge shape of the electrode body 15. The knife 11 is therefore wider at the upper side in FIG. 3*b* than the lower one. Additionally, the width of the knife 11 in FIG. 3*a* is smaller than the height so that one narrow side 24 is formed at each of the top and the bottom. The knife 11 therefore shows a form resembling the shape of a mechanically cutting knife, with the narrow sides 24 being equivalent to the blade and/or the back of said knife and the flat sides 23 the side surfaces of the knife blade. Due to the form the flat sides 23 have an incline that is not equal to 0° so that the extension of the flat sides 23 intersect and in FIG. 3*b* the upper narrow side 24 encloses an angle with each of the flat sides 23 which is smaller than 90°.

The electrode bodies 14, 15, and 16 are formed from stainless steel. The adhesion of tissue at the metallic surface can be avoided by a sectionally applied silver coating or by an application or coating of a silver alloy. The electrode bodies could also be made entirely from a material having a high thermal conductivity, e.g., gold, silver, platinum, or an alloy of these materials, nickel, or a nickel alloy, or copper or a copper alloy. Particularly electrode bodies made from copper should be provided with a bio-compatible layer at their surfaces coming into contact with the tissue. It could also be advantageous to produce the electrode bodies 14 and 16 only from a material having a high thermal conductivity in order to reduce the adhesion of tissue to the exterior edges and to improve the function of cutting in general. The explanations of this paragraph regarding the selection of materials appropriately apply for all electrode bodies described in this application, thus particularly for the electrode bodies 14, 15, 16, 32, 34, and 36 in the description of the figures.

Therefore, electrode surfaces 25, 26, 27, and 28 are formed at the exterior surfaces of the electrode bodies 14, 15, and 16, representing the contact surfaces for the cutting or coagulation current flowing through contacting tissue. As discernible from FIG. 3*b* the area of the first electrode surface 25 of the central, first electrode body 15, essentially formed by the two lateral sides of the acute edge 22, projecting from the body of the instrument insert 6 beyond the first electrode surfaces 26 of the exterior second electrode bodies 14 and 16, is considerably smaller than the adjacent first electrode surfaces 26 of the second electrode bodies 14 and 16 combined, extending into the lower narrow side 24. Additionally, the cross-section of the acute edge 22 is provided at its tip with a strongly curved contour, at which the electric flux lines approach each other in a stellar or radiant form. This way at the lower narrow side an uneven pair of electrodes is formed at which the effective electrode surface 25 of the first central electrode body 15 represents the preferred starting point for the embodiment of a cutting current. Therefore, the lower narrow side 24 is embodied for cutting.

The area of the second electrode surfaces 28 combined is approximately as large as the area of the second electrode surface 27. Thus, the upper narrow side 24 is suitable for coagulation.

The instrument inserts according to FIGS. 2b and 2c show a cross-section in the area of their blades each resembling the cross-section according to FIG. 3b.

FIG. 4a shows the instrument insert 6 according to FIG. 2b with a saber-like curved knife 11. Together with the insulation layers 17 arranged between them the electrode bodies 14, 15, and 16 form, in the area of the knife 11, a structural unit in the form of a layered package having a sandwich structure. The wedge-shaped electrode body 15 is aligned outwards with its acute edge 22, thus pointing away from the virtual center of the curvature of the knife 11. However, the electrode bodies 14 and 16 show a cross-section, although tapering inwardly, i.e. towards the center of the curvature of the knife 11, however, overall a knife 11 results having a width reducing towards the outside so that the acute edge 22 with the adjacent electrode bodies 14 and 16 form the blade of the knife 11 at the exterior edge 18, while at the interior edge 19, by the wider back 21 of the electrode body 15 and the electrode surfaces of the electrode bodies 14 and 16 extending on the interior edge 19, a wider support forms provided with good coagulation properties. By the saber-like knife form, giving the instrument insert 6 overall the form of a hockey stick, the tissue layers can be separated and individually picked up for treatment.

FIG. 4b shows an instrument insert 6 with a reverse alignment of the knife 11. Now, the wider end of the cross-section of the knife is arranged at the exterior edge 18, while the blade of the knife 11, i.e. the narrower end of the cross-section of the blade, is embodied at the interior edge 19. Thus, the instrument insert 6 according to FIG. 4b differs from the instrument insert 6 according to FIG. 4a only in that the curved shape of the knife 11 is embodied towards the side of the blade such that the virtual center of the curvature is located at the side the back 21 of the central, wedge-shaped electrode body 15 points to. This way, tissue, for example vessels of body fluids, can be picked up and electro-surgically cut or separated by this instrument insert 6, while coagulation can be performed by movements similar to dabbing.

FIG. 5a shows another exemplary embodiment of an instrument insert 6. At the distal end of the shaft 5, a projection 29 is provided, which accepts the lateral surface 20 enlarged in reference to the exemplary embodiment according to FIG. 2a perpendicularly in reference to the longitudinal direction of the shaft 5. As discernible in FIG. 5c, which illustrates a cross-section through the knife 11 along the plane B-B in FIG. 5b, this enlarged lateral surface 20 of the electrodes 14 and 16, embodied mirror-symmetrical in reference to each other, renders the width of the narrow sides 24 comparatively smaller in reference to the width of the flat sides 23 and a form results even more resembling a knife blade, with the two flat sides 23 forming the lateral surfaces of the knife blade while the two narrow sides 24 form the blade and the back of the knife. The first electrode surfaces 26 and the second electrode surfaces 28 of the second electrode bodies 14 and 16 extend beyond the edges 43 into the narrow sides 24 of the knife 11 and together with the first electrode surface 25 each form a pair of electrodes at the acute edge 22 and/or the second electrode surface 27 at the back 21 of the first electrode body 15, provided for cutting and/or coagulation.

The connections in the shaft 5 of the instrument insert 6 according to FIGS. 5a through 5c are guided such that this instrument insert 6 can be inserted into the same insert seat 4 in which the instrument insert 6 according to FIGS. 3a and 3b also fits, for example.

FIG. 6a shows another exemplary embodiment of an instrument insert 6 with a spatula-shaped knife 11. At the facial side 30 of the distal end 7 it is discernible that the central first electrode body 15 forming the back 21 extends not over the entire lateral extension, i.e. the height of the knife 11. The cross-sectional illustration shown in FIG. 6c along the plane C-C in FIG. 6b shows that the insulation layer 17 is formed in one piece with an approximately H-shaped cross-section and the first electrode 31, i.e. the electrode encompassing the central first electrode body 15, is divided into two parts of a structural unit by the insulation layer 17. The second part of the first electrode 31 is formed by the tip 32 extending in the longitudinal direction of the knife 11 and electrically connected to the first electrode body 15 at the proximal end. This tip 32 or 22 projects beyond the electrode surfaces 26 extending into the narrow sides of the electrode bodies 14 and 16 forming the second electrode 32 or 22 and thus form the preferred starting point for the embodiment of the cutting current.

As shown in FIG. 7c, instead of the tip 32 according to FIG. 6c, a round wire 34 can also be used, which is embedded in the insulation layer 17 along a circumferential segment not exceeding a semicircle. This wire thus offers a first electrode surface 25 of the first electrode 31, having a contour extending curved in the cross-section and thus bundling or concentrating the incoming and/or outgoing electric flux lines. Therefore, in the exemplary embodiments according to FIGS. 6a, 6b, and 6c and/or 7a, 7b, and 7c both first as well as the second electrodes are embodied in two parts with the components, i.e. the electrode bodies 14 and 16 and/or 15 and 32 are electrically connected at the proximal end.

FIG. 8a shows an exemplary embodiment of an instrument insert 6, in which the knife 11 is formed by an electrode 31 embodied in two parts and a second electrode 33 embodied in one part. The second electrode is therefore formed by an electrode body 14 having a rectangular base body in its cross-section, into which at two diagonally opposite edges 43 recesses 35 are inserted extending longitudinal in reference to the knife, each being off-set in reference to each other and rectangular in their cross-section. The electrode body 14 therefore has an approximately Z-shaped progression in the cross-section. One electrode body 15 and 36 is inserted each into the recesses 35, electronically separated from the electrode body 14 of the second electrode 33 by an insulating layer 27.

The electrode body 15 is connected electrically conductive to the electrode body 36 at the proximal end, and both electrode bodies 15 and 36 thus form a common electrode. By the narrow shape and the arrangement of the electrode body 15 it is achieved that its narrow side forms a first electrode surface 25 at the narrow side 24 of the knife 11 and a flat side forms a second electrode surface 27 at the flat side 23 of the knife 11, with the electrode surface 27 covering approximately half the flat side 23 and being several times larger than the first electrode surface 25. The first electrode surface 25 of the electrode body 15 is further smaller by a multiple than the first electrode surface 26 formed by the remaining base body of the electrode body 14 on a narrow side 24, being the upper one in FIG. 8c, resulting in said first electrode surface 26 together with the first electrode surface 25 of the first electrode body 15 forming an pair of electrodes for cutting.

The left flat side 23 in FIG. 8c is however longitudinally divided approximately in half by the projecting insulating layer 17 rendering the second electrode surface 27 of the electrode body 15 approximately of the same size as the second electrode surface 28 of the electrode body 14 formed at the same flat side 23. Therefore, this way a pair of electrodes is formed having good coagulation properties. First and second electrode surfaces 25 and 27 and/or 26 and 28 are each separated from each other by longitudinally extending edges 43.

The electrode body 36 is formed and arranged similar to the electrode body 15 such that overall a cross-section results, in its entirety rotationally symmetrical by 180°, thus forming to additional pairs of electrodes as described, one for cutting and one for coagulating.

Therefore, the knife 11 has two blades, and coagulation is performed by tipping the instrument around a longitudinal axis of the knife 11 by a quarter rotation, thus by placing a flat side 23 of the knife 11 onto the tissue.

The connections in the shaft 5 of the instrument insert 6 according to FIGS. 8a through 8c are guided such that this instrument insert 6 can be inserted into the same insert seat 4 in which the instrument insert 6 according to FIGS. 3a and 3b fits, for example.

In the exemplary embodiment according to FIG. 9a, the second electrode 33 is formed by an electrode body 37 embodied in one piece, which in the area of the knife 11 converts into two legs 14 and 16 forming electrode bodies. These legs 14 and 16 are arranged like the prongs of a tuning fork and in the area of the shaft 5 are connected in a connection section 38 equivalent to a handle of a tuning fork. By this connection section 38 the electrode bodies 14 and 16 are held together perpendicularly in reference to the longitudinal direction, thus in the direction of layer sequence of the sandwich-structure. Additional screws, rivets, or bars can be waived, however (they may) additionally increase the stability against mechanical bending stress or impacts.

The electrode bodies 14 and 16 leave a space between each other, approximately V-shaped in its cross-section, in which the wedge-shaped electrode body 15 is inserted, with an insulating layer 17 being provided, creating a structural unit, between on the one hand, the electrode bodies 14 and 16 and, on the other hand, the electrode body 15. The acute edge 22 of the electrode body slightly projects from the otherwise planar embodied bottom of the knife 11 and forms the electro-surgically effective blade, particularly the active cutting electrode. At the upper side, i.e. the back of the knife, the surface of the knife body is divided by the insulating layer 17 into sections forming the electrode surfaces 27 and 28 of another pair of electrodes. Due to the fact that the totals of the electrode surfaces 28 are identical with regard to their area to the electrode surface 27 coagulation can be performed with this pair of electrodes. The electrode surfaces 27 and 28 align towards each other and end at the insulating layer 17 so that, equivalent to the other exemplary embodiments according to FIGS. 2a through 7c, an overall smooth surface of the back of the knife 11 results for coagulation.

FIG. 9c shows a cross-section along the plane A-A. By a comparison with FIGS. 5c, 6c, and 7c it is discernible that the instrument inserts according to FIGS. 2a through 7c can also be provided with a base body shaped like a tuning fork comprising the electrode bodies 14 and 16 of the second electrode 33.

In the exemplary embodiment according to FIGS. 9a through 9d, in the area of the shaft 5, as discernible in FIG. 9d, a groove 39 is inserted into the upper side, i.e. the side facing away from the blade or the extension of the back of the knife 11, which accepts the connection line 41 for the first electrode enclosed in an insulating cover 40.

The exemplary embodiments according to FIGS. 2a through 9c have in common that the distal end 7 of the effective area 8, i.e. the knife 11, is always embodied in a rounded fashion, with the faces 30 of the distal end, rounded by said curves, being penetrated by the respective electrode bodies 14, 15, 16 and/or 36, and the insulating layers 17 such that the cross-section of the respective knife 11 is shown. Thus, with the face 30 of the distal end, to a certain extent, coagulation can be performed.

In the exemplary embodiment according to FIGS. 8a through 8c, for the production of another exemplary embodiment, the electrode bodies 15 and 36 can be formed at a common base body shaped like a tuning fork, with the connection line for the second electrode 33 being guided along said base body in a groove.

In additional exemplary embodiments, one described instrument insert 6 each is connected to the instrument body 2 in a fixed and non-detachable manner.

In the electro-surgical instrument 1, two electrode surfaces 25, 27 are embodied at a first electrode, having different sizes, each of which forming a pair of electrodes together with electrode surfaces 26, 28 of a second electrode, with the smaller electrode surface 25 of the first electrode can be used as the active electrode for cutting and the larger electrode surface 27 of the first electrode for coagulation. During operation the electrodes are connected to a two-pole outlet of a commercial generator, which can switch between two output signals for cutting and coagulating. A layered, stacked structure of the effective section of the instrument comprising electrode bodies with interposed insulation layers allows a design resembling the shape of a knife, a spatula, or a blade.

The invention claimed is:

1. An electro-surgical instrument for high-frequency cutting and high-frequency coagulation comprising two electrodes (31, 33) spaced apart from each other by insulating material (17), and during operation connected at a proximal end (9) of the instrument (1) to an outlet of a high-frequency supply device, with a first electrode surface (25) of a first electrode (15, 31, 32, 34, 36) being provided such that together with a second electrode (14, 16, 33) it can be used for a cutting operation, the first electrode (15, 31, 32, 34, 36) comprises a second electrode surface (27) that can be used together with the second electrode (14, 16, 33) for a coagulation operation, and an effective area of the first electrode surface (25) of the first electrode (15, 31, 32, 34, 36) is smaller than an effective area of the second electrode surface (27) of the first electrode (15, 31, 32, 34, 36), wherein the first electrode (15, 31, 32, 34, 36) is fixedly connected to the second electrode (14, 16, 33) by at least one electrically insulating layer (17) fixed therebetween in a sandwich structure and forms a knife (11) of the electro-surgical instrument (1), and layers of the sandwich structure formed by the first and second electrodes and the insulating layer are aligned longitudinally in reference to sides (20, 23) of the knife (11).

2. An electro-surgical instrument according to claim 1, wherein the second electrode (14, 16, 33) comprises a first electrode surface (26) with an effective area that is larger than the effective area of the first electrode surface (25) of the first electrode (15, 31, 32, 34, 36) and the first electrode surface (26) of the second electrode (14, 16, 33) together with the first electrode surface (25) of the first electrode (15, 31, 32, 34, 36) can be used as a neutral electrode for high-frequency cutting.

3. An electro-surgical instrument according to claim 1, wherein a second electrode surface (28) of the second electrode (14, 16, 33) has an effective area essentially of equal size as the effective area of the second electrode surface (27) of the first electrode (15, 31, 32, 34, 36) and the second electrode surface (28) of the second electrode (14, 16, 33) can be used together with the second electrode surface (27) of the first electrode (15, 31, 32, 34, 36) as a pair of electrodes for high-frequency coagulation.

4. An electro-surgical instrument according to claim 1, wherein an area of a first electrode surface (26) of the second electrode (14, 16, 33) and a second electrode surface (28) of the second electrode (14, 16, 33) are identical.

5. An electro-surgical instrument according to claim 1, wherein the first electrode surface (25) of the first electrode (15, 31, 32, 34, 36) and the second electrode surface (27) of the first electrode (15, 31, 32, 34, 36) are formed on a common base body.

6. An electro-surgical instrument according to claim 5, wherein the base body of the first electrode (15, 31, 32, 34, 36) comprises an electrically conductive electrode body (15).

7. An electro-surgical instrument according to claim 1, wherein a first electrode surface (26) of the second electrode (14, 16, 33) and a second electrode surface (28) of the second electrode (14, 16, 33) are formed on a common base body.

8. An electro-surgical instrument according to claim 7, wherein the base body of the second electrode (14, 16, 33) comprises an electrically conductive electrode body (36, 38).

9. An electro-surgical instrument according to claim 1, wherein the knife (11) of the electro-surgical instrument (1) is shaped as a spatula.

10. An electro-surgical instrument according to claim 9, wherein the knife (11) of the electro-surgical instrument (1) is formed in a shape of a saber or curved like a hook.

11. An electro-surgical instrument according to claim 1, wherein the knife (11) has a back (21) and a blade (22) and the back (21) is wider than the blade (22).

12. An electro-surgical instrument according to claim 1, wherein the first electrode surface (25) of the first electrode (15, 31, 32, 34, 36) is arranged at an exterior edge (18) of the knife (11) which is curved.

13. An electro-surgical instrument according to claim 1, wherein the first electrode surface (25) of the first electrode (15, 31, 32, 34, 36) is arranged at an interior side (19) of the knife (11) which is curved.

14. An electro-surgical instrument according to claim 1, wherein the first electrode surface (25) of the first electrode (15, 31, 32, 34, 36) and a second electrode surface (27) of the first electrode (15, 31, 32, 34, 36) are arranged at opposite edges (24) of the knife (11).

15. An electro-surgical instrument according to claim 14, wherein the second electrode surface (27) of the first electrode (15, 31, 32, 34, 36) is arranged at least at one side (20, 23) of the knife (11).

16. An electro-surgical instrument according to claim 1, wherein lateral sides of the knife are formed at least partially by electrode bodies of the second electrode.

17. An electro-surgical instrument according to claim 16, wherein the second electrode (14, 15, 33) has two electrode bodies (14, 16) that are mirror-symmetrical in reference to a plane, and the two electrode bodies (14, 16) of the second electrode (14, 16, 33) are arranged at both sides of the first electrode (15, 31, 32, 34) perpendicularly in reference to a longitudinal direction of the instrument.

18. An electro-surgical instrument according to claim 16, wherein the electrode bodies (14, 16) of the second electrode (14, 16, 33) each form one prong of an electrically conductive body shaped in one piece like a tuning fork.

19. An electro-surgical instrument according to claim 1, wherein a perimeter of a cross-section of the first electrode (15, 31, 32, 34, 36) defines a wedge, a section around an acute edge (22) of the wedge forms the first electrode surface (25) of the first electrode (15, 31, 32, 34, 36), a back (21) of the wedge forms the second electrode surface (27), and the first electrode (15, 31, 32, 34, 36) is arranged between two electrode bodies (14, 16) of the second electrode (14, 16, 33).

20. An electro-surgical instrument according to claim 19, wherein the electrode bodies (14, 16) of the second electrode (14, 16, 33) are connected in one piece.

21. An electro-surgical instrument according to claim 1, wherein the instrument (1) has two narrow sides (24) arranged opposite each other and two flat surfaces (23) arranged opposite each other, a first flat side (23) and a first narrow side (24) enclose an angle of 90° or less, and the flat sides (23) are each formed by an electrode body (14, 16) of the second electrode (14, 16, 33), the electrode bodies (14, 16) of the second electrode are provided with electrode surfaces (26, 28) partially extending into the narrow sides (24), the first electrode (15, 31, 32, 34) has an electrode body (15, 32, 34) defining a wedge-shaped perimeter in cross-section, the electrode body (15, 32, 34) of the first electrode (15, 31, 32, 34) is arranged between the electrode bodies (14, 16) of the second electrode (14, 16, 33) and spaced apart therefrom by the insulating material, an acute edge (22) of the electrode body (15, 32, 34) of the first electrode, wedge-shaped in its cross-section, projects from a narrow side (24), and a back (21) of the electrode body (15, 32, 34) of the first electrode, wedge-shaped in its cross-section, forms a part of an opposite one of the narrow sides (24), so that cutting can be achieved with one of the narrow sides (24) and that coagulation can be achieved with the other of the narrow sides (24).

22. An electro-surgical instrument according to claim 21, wherein the electrode body (15) of the first electrode (15, 33) is embodied in one piece and fills the perimeter of the wedge-shaped cross-section.

23. An electro-surgical instrument according to claim 21, wherein the flat sides (23) have an angle in reference to each other measuring less than 45°.

24. An electro-surgical instrument according to claim 21, wherein the back (21) of the wedge-shaped electrode body (15, 32, 34) of the first electrode (15, 31, 32, 34) is arranged at the first narrow side (24).

25. An electro-surgical instrument according to claim 21, wherein the first electrode surface (25) of the first electrode (15, 31, 32, 34, 36) defines an at least sectionally curved contour in cross-section.

26. An electro-surgical instrument according to claim 21, wherein the first electrode surface (25) of the first electrode (15, 31, 32, 34) comprises a wire (34) embedded in the insulating material (17).

27. An electro-surgical instrument according to claim 21, wherein the first electrode (15, 31, 32, 34, 36) with the first electrode surface (25) projects from the instrument body (11) beyond an electrode surface (26) of the second electrode (14, 16, 33) for use in high-frequency cutting.

28. An electro-surgical instrument according to claim 1, wherein the second electrode (14, 33) is formed from a base body (14), that in cross-section essentially forms a rectangle, the base body is provided with a recess (35) at least at one edge (43), and the electrode body (15, 36) of the first electrode (15, 31, 36) is inserted in the recess, separated by an insulating layer from the second electrode (14, 33), the electrode body (15, 36) of the first electrode (15, 31, 36) has a first electrode surface (25) that along with a side of the second electrode forms the pair of electrodes for high-frequency cutting along a shorter side (24) of the rectangle, and the electrode body (15, 36) of the first electrode (15, 31, 36) has a second electrode surface (27), that along with a longer side of the second electrode (14), forms a pair of electrodes for high-frequency coagulation.

29. An electro-surgical instrument according to claim 28, wherein the instrument (1) has two opposite narrow sides (24) and two opposite flat sides (23), arranged perpendicularly offset in reference thereto, each of which is formed at least partially by the narrow side (24) and the flat side (23) of a narrow electrode body (15, 36) of the first, cutting electrode (15, 31, 36), that two such narrow electrode bodies (15, 36) are arranged offset in reference to each other, and that the electrode body (14) of the second, neutral electrode (14, 33) extends approximately Z-shaped between the narrow electrode bodies (15, 36) and is spaced apart therefrom by the insulating material (17) such that both narrow sides (24) can cut and both flat sides (23) can coagulate.

30. An electro-surgical instrument according to claim 29, wherein the electrode body (15, 32, 34, 36) of the first electrode (15, 31, 32, 34, 36) is connected in one piece at the proximal end (9).

31. An electro-surgical instrument according to claim 1, wherein the electrode surface (27) of the first electrode (15, 31, 32, 34, 36) effective during coagulation has an area amounting between two thirds and one-and-one half times an area of the electrode surface (28) of the second electrode (14, 16, 33) effective during coagulation.

32. An electro-surgical instrument according to claim 1, wherein the electrode surface (27) of the first electrode (15, 31, 32, 34, 36) effective during coagulation has an area ranging from 0.9 to 1.1 times the area of the effective electrode surface (28) of the second electrode (14, 16, 33) effective during coagulation.

33. An electro-surgical instrument according to claim 1, wherein the electrode surface (27) of the first electrode (15, 31, 32, 34, 36) effective during coagulation has an area equivalent to an area of the electrode surface (28) of the second electrode (14, 16, 33) effective during coagulation.

34. An electro-surgical instrument according to claim 1, wherein the electrode surface (26) of the second electrode (14, 16, 33) effective during cutting has an area at least one-and-one half times an area of the electrode surface (25) of the first electrode (15, 31, 32, 34, 36) effective during cutting.

\* \* \* \* \*